US010767108B2

(12) United States Patent
Armstrong et al.

(10) Patent No.: US 10,767,108 B2
(45) Date of Patent: Sep. 8, 2020

(54) PERFLUOROETHER-STABILIZED QUANTUM DOTS

(71) Applicant: 3M INNOVATIVE PROPERTIES COMPANY, St. Paul, MN (US)

(72) Inventors: Paul B. Armstrong, St. Paul, MN (US); Zai-Ming Qiu, Woodbury, MN (US); Karissa L. Eckert, Ham Lake, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 185 days.

(21) Appl. No.: 15/745,749

(22) PCT Filed: Aug. 10, 2016

(86) PCT No.: PCT/US2016/046283
§ 371 (c)(1),
(2) Date: Jan. 18, 2018

(87) PCT Pub. No.: WO2017/030857
PCT Pub. Date: Feb. 23, 2017

(65) Prior Publication Data
US 2018/0208835 A1    Jul. 26, 2018

Related U.S. Application Data

(60) Provisional application No. 62/209,508, filed on Aug. 25, 2015, provisional application No. 62/206,932, filed on Aug. 19, 2015.

(51) Int. Cl.
*C09K 11/02* (2006.01)
*B32B 7/12* (2006.01)
(Continued)

(52) U.S. Cl.
CPC .............. *C09K 11/025* (2013.01); *B32B 7/12* (2013.01); *B32B 27/08* (2013.01); *B32B 27/36* (2013.01);
(Continued)

(58) Field of Classification Search
None
See application file for complete search history.

(56) References Cited

U.S. PATENT DOCUMENTS 6,949,206 B2    9/2005    Whiteford
7,018,713 B2    3/2006    Padiyath
(Continued)

FOREIGN PATENT DOCUMENTS

JP        2015127733        7/2015
WO    WO 2005-022120    3/2005
(Continued)

OTHER PUBLICATIONS

Kasi, "Perfluoropolyethers With Acid End Groups: Amphiphilicity and Emulsification", Journal of Applied Polymer Science, vol. 57, Dec. 31, 1995, pp. 797-809.
(Continued)

*Primary Examiner* — Jeffrey D Washville
(74) *Attorney, Agent, or Firm* — Kent S. Kokko; Lisa P. Fulton

(57) ABSTRACT

A composite particle comprising a fluorescent core/shell nanoparticle and a perfluoroether ligand bound the surface thereof is described.

21 Claims, 2 Drawing Sheets

(51) Int. Cl.

| | | |
|---|---|---|
| *B32B 7/08* | (2019.01) | |
| *B32B 27/36* | (2006.01) | |
| *C07C 319/18* | (2006.01) | |
| *H05B 33/14* | (2006.01) | |
| *H05B 33/20* | (2006.01) | |
| *C07C 327/28* | (2006.01) | |
| *C09K 11/56* | (2006.01) | |
| *C09K 11/70* | (2006.01) | |
| *B32B 27/08* | (2006.01) | |
| *F21V 8/00* | (2006.01) | |
| *B82Y 20/00* | (2011.01) | |
| *B82Y 40/00* | (2011.01) | |
| *G02F 1/13357* | (2006.01) | |

(52) U.S. Cl.
CPC .......... *C07C 319/18* (2013.01); *C07C 327/28* (2013.01); *C09K 11/02* (2013.01); *C09K 11/565* (2013.01); *C09K 11/70* (2013.01); *C09K 11/703* (2013.01); *H05B 33/14* (2013.01); *H05B 33/20* (2013.01); *B32B 2250/02* (2013.01); *B32B 2250/244* (2013.01); *B32B 2250/40* (2013.01); *B32B 2255/10* (2013.01); *B32B 2255/26* (2013.01); *B32B 2307/422* (2013.01); *B32B 2457/202* (2013.01); *B82Y 20/00* (2013.01); *B82Y 40/00* (2013.01); *G02B 6/005* (2013.01); *G02B 6/0096* (2013.01); *G02F 1/133615* (2013.01); *G02F 2001/133614* (2013.01); *G02F 2202/36* (2013.01); *Y10S 977/774* (2013.01); *Y10S 977/818* (2013.01); *Y10S 977/824* (2013.01); *Y10S 977/892* (2013.01); *Y10S 977/95* (2013.01)

(56) References Cited

U.S. PATENT DOCUMENTS

| | | | |
|---|---|---|---|
| 7,267,875 | B2 | 9/2007 | Whiteford |
| 8,283,412 | B2 | 10/2012 | Liu |
| 8,848,132 | B2 | 9/2014 | O'Neill |
| 8,901,333 | B2 | 12/2014 | Tulsky |
| 2005/0117868 | A1 | 6/2005 | Chen |
| 2010/0233094 | A1* | 9/2010 | Chung .................. C09K 11/02 424/9.32 |
| 2011/0110867 | A1* | 5/2011 | Chung ............... A61K 49/0002 424/9.37 |
| 2014/0027711 | A1 | 1/2014 | Breen |
| 2014/0079912 | A1 | 3/2014 | Euliss |
| 2014/0287248 | A1 | 9/2014 | Flynn |

FOREIGN PATENT DOCUMENTS

| | | |
|---|---|---|
| WO | WO 2009-051337 | 4/2009 |
| WO | WO 2015-095032 | 6/2015 |
| WO | WO 2015-095296 | 6/2015 |
| WO | WO 2015-138174 | 9/2015 |
| WO | WO 2015-153148 | 10/2015 |
| WO | WO 2016-081219 | 5/2016 |
| WO | WO 2016-167927 | 10/2016 |
| WO | WO 2016-168048 | 10/2016 |

OTHER PUBLICATIONS

Alivisatos, "Semiconductor clusters, nanocrystals, and quantum dots", Science, Feb. 1996, vol. 271, pp. 933-937.
Dabbousi, "(CdSe)ZnS Core—Shell Quantum Dots: Synthesis and Characterization of a Size Series of Highly Luminescent Nanocrystallites", Journal of Physical Chemistry B, Nov. 1997, vol. 101, No. 46, pp. 9463-9475.
Gorelikov, "Silica-Coated Quantum Dots for Optical Evaluation of Perfluorocarbon Droplet Interactions with Cells", Langmuir, 2011, vol. 27, pp. 15024-15033.
Hines, "Synthesis and Characterization of Strongly Luminescing ZnS-Capped CdSe Nanocrystals", Journal of Physical Chemistry, Jan. 1996, Vo. 100, pp. 2, pp. 468-471.
Murray, "Synthesis and characterization of nearly monodisperse CdE (E=sulfur, selenium, tellurium) semiconductor nanocrystallites," Journal of American Chemical Society, 1993, vol. 115, No. 19, pp. 8706-8715.
Parker, "Electrostatically Directed Self-Assembly of Ultrathin Supramolecular Polymer Microcapsules", Advanced Functional Materials, 2015, vol. 25, pp. 4091-4100, XP002763753.
Peng, "Epitaxial growth of highly luminescent CdSe/CdS Core/Shell nanocrystals with photostability and electronic accessibility," Journal of American Chemical Society, 1997, vol. 119, No. 30, pp. 7019-7029.
Saunders, "Solvent Density-Dependent Steric Stabilization of Perfluoropolyether-Coated Nanocrystals in Supercritical Carbon Dioxide", Journal of Physical Chemistry B, Oct. 2004, vol. 108, No. 41, pp. 15969-15975, XP008149833.
Shah, "Single-Step Self-Organization of Ordered Macroporous Nanocrystal Thin Films", Advanced Materials, Jun. 2003, vol. 15, No. 12, pp. 971-974, XP002763752.
International Search Report for PCT International Application No. PCT/US2016/046283, dated Nov. 11, 2016, 5 pages.

* cited by examiner

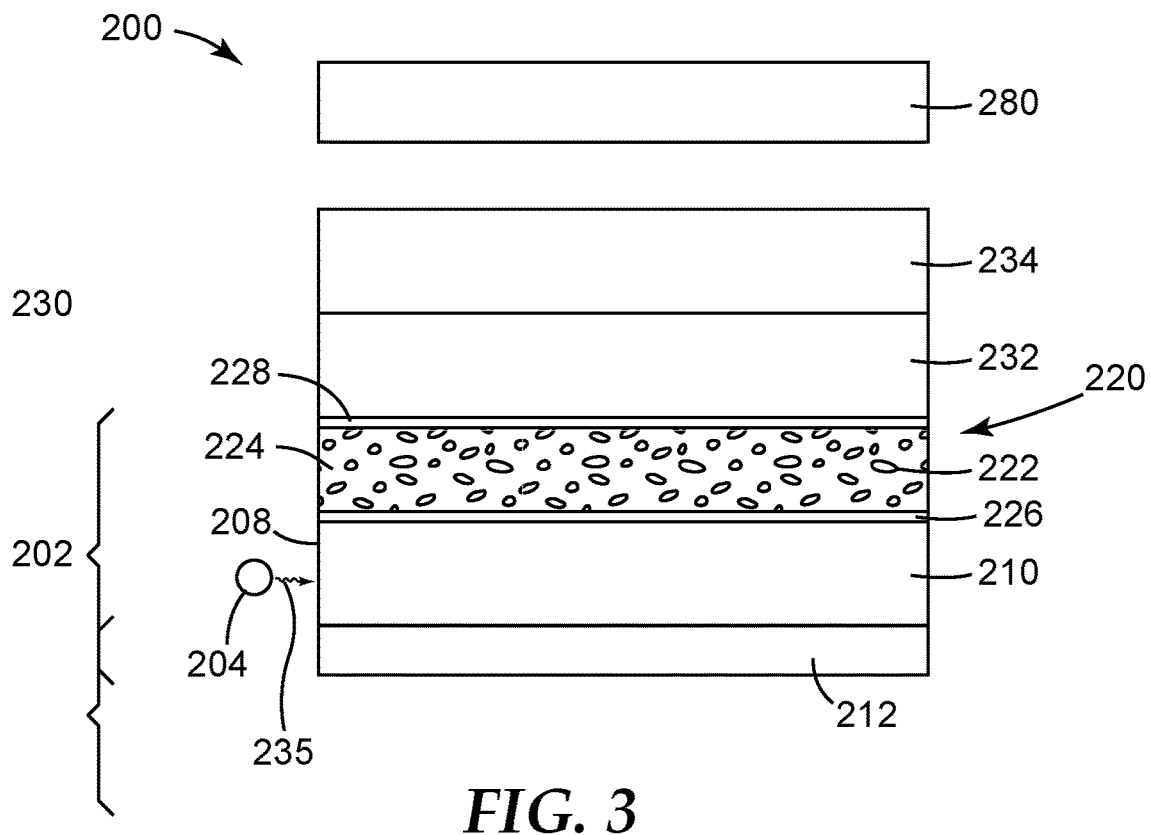
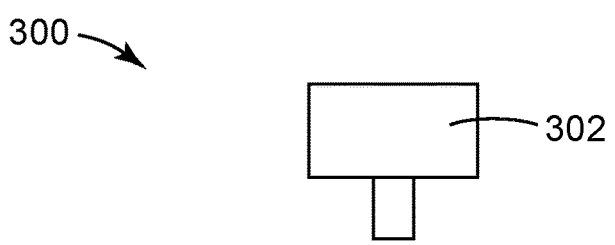
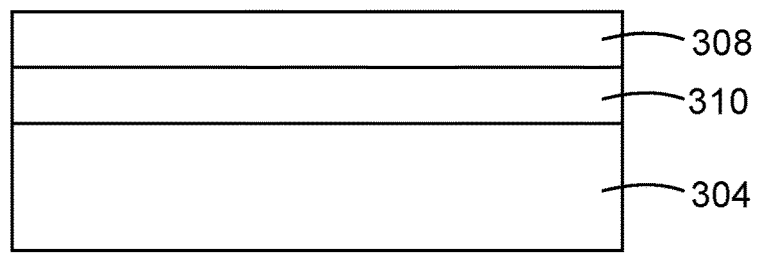
FIG. 4

PERFLUOROETHER-STABILIZED QUANTUM DOTS

CROSS REFERENCE TO RELATED APPLICATIONS

This application is a national stage filing under 35 U.S.C. 371 of PCT/US2016/046283, filed Aug. 10, 2016, which claims the benefit of U.S. Application No. 62/206,932, filed Aug. 19, 2015 and U.S. Application No. 62/209,508, filed Aug. 25, 2015, the disclosures of which are incorporated by reference in their entirety herein.

BACKGROUND

Quantum Dot Enhancement Films (QDEF) are used as the light source for LCD displays. Red and green quantum dots are used in QDEF with a blue LED as the light source to give the full spectrum of colors. This has the advantage of improving the color gamut over the typical LCD display and keeping the energy consumption low compared to OLED displays.

Once the quantum dots are synthesized, they are treated with an organic ligand that binds to the exterior surface of the quantum dot. Colloidal quantum dot nanoparticles (preferably, nanocrystals) that are stabilized with organic ligands can have improved quantum yields due to passivating surface traps, controlling dispersion stability in a carrier fluid and/or polymer matrix, stabilizing against aggregation and degradation, and influencing the kinetics of nanoparticle (preferably, nanocrystal) growth during synthesis. Therefore, optimizing the organic ligand is important for achieving optimal quantum yield, processability, and functional lifetime in QDEF.

SUMMARY

In one aspect, the present disclosure provides a composite particle that includes: a fluorescent semiconductor core/shell nanoparticle (preferably nanocrystal); and a fluorinated ligand attached to the core/shell nanoparticle outer surface, the ligand of the formula:

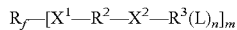

wherein
$R_f$ is a perfluoroether group,
$R^2$ is a hydrocarbyl group including alkylene, arylene, alkarylene and aralkylene;
$R^3$ is a hydrocarbyl group including alkylene, arylene, alkarylene and aralkylene;
$X^1$ is $-CH_2-O-$, $-CO_2-$, $-CONR^1-$, or $-SO_2NR^{1-}$ where $R^1$ is H or $C_1$-$C_4$ alkyl;
$X^2$ is a covalent bond, $-S-$, $-O-$ or $-NR^1-$, $-CONR^1-$, or $-SO_2NR^{1-}$ where $R^1$ is H or $C_1$-$C_4$ alkyl;
n at least one;
m is 1 or 2
L is an ligand group selected from $-CO_2H$, $-SH$, $-P(O)(OH)_2$, $-P(O)OH$, $-NH_2-OH$, and $-SO_3H$. In some preferred embodiments, the ligand of Formula I has at least two L ligand groups.

In one aspect, the present disclosure provides a composite particle that includes: a fluorescent semiconductor core/shell nanoparticle (preferably, nanocrystal); and a ligand of Formula I attached to the core/shell nanoparticle outer surface. The fluorescent semiconductor core/shell nanoparticle includes: an InP core; an inner shell overcoating the core, wherein the inner shell includes zinc selenide and zinc sulfide; and an outer shell overcoating the inner shell, wherein the outer shell includes zinc sulfide. In another aspect, the ligand functional composite particle further comprises a fluid carrier.

The composite particles can be used in coatings and films for use in optical displays. The fluorescent semiconductor nanoparticles emit a fluorescence signal at a second wavelength of light when excited by a first wavelength of light that is shorter than the second wavelength of light.

As used herein:

The term "alkyl" refers to a monovalent group that is a radical of an alkane and includes straight-chain, branched, and cyclic alkyl groups, including both unsubstituted and substituted alkyl groups. Unless otherwise indicated, the alkyl groups typically contain from 1 to 30 carbon atoms. In some embodiments, the alkyl groups contain 1 to 20 carbon atoms, 1 to 10 carbon atoms, 1 to 6 carbon atoms, 1 to 4 carbon atoms, or 1 to 3 carbon atoms. Examples of "alkyl" as used herein includes, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, norbornyl, and the like. Unless otherwise noted, alkyl groups may be mono- or poly-valent.

The term "alkylene" refers to a divalent group that is a radical of an alkane and includes groups that are linear, branched, cyclic, bicyclic, or a combination thereof. Unless otherwise indicated, the alkylene group typically has 1 to 30 carbon atoms. In some embodiments, the alkylene group has 1 to 20 carbon atoms, 1 to 10 carbon atoms, 1 to 6 carbon atoms, or 1 to 4 carbon atoms.

The term "aryl" refers to a monovalent group that is aromatic and, optionally, carbocyclic. The aryl has at least one aromatic ring. Any additional rings can be unsaturated, partially saturated, saturated, or aromatic. Optionally, the aromatic ring can have one or more additional carbocyclic rings that are fused to the aromatic ring. Unless otherwise indicated, the aryl groups typically contain from 6 to 30 carbon atoms. In some embodiments, the aryl groups contain 6 to 20, 6 to 18, 6 to 16, 6 to 12, or 6 to 10 carbon atoms. Examples of an aryl group include phenyl, naphthyl, biphenyl, phenanthryl, and anthracyl.

Heteroaryl is aryl containing 1-3 heteroatoms such as nitrogen, oxygen, or sulfur and can contain fused rings. Some examples of heteroaryl are pyridyl, furanyl, pyrrolyl, thienyl, thiazolyl, oxazolyl, imidazolyl, indolyl, benzofuranyl, and benzthiazolyl. Unless otherwise noted, aryl and heteroaryl groups may be mono- or poly-valent.

The term "arylene" refers to a divalent group that is aromatic, and optionally carbocyclic. The arylene has at least one aromatic ring. Any additional rings can be unsaturated, partially saturated, or saturated. Optionally, an aromatic ring can have one or more additional carbocyclic rings that are fused to the aromatic ring. Arylene groups often have 6 to 20 carbon atoms, 6 to 18 carbon atoms, 6 to 16 carbon atoms, 6 to 12 carbon atoms, or 6 to 10 carbon atoms.

The term "aralkyl" refers to a monovalent group that is an alkyl group substituted with an aryl group. The term "alkaryl" refers to a monovalent group that is an aryl substituted with an alkyl group. For both groups, the alkyl portion often has 1 to 10 carbon atoms, 1 to 6 carbon atoms, or 1 to 4 carbon atoms and an aryl portion often has 6 to 20 carbon atoms, 6 to 18 carbon atoms, 6 to 16 carbon atoms, 6 to 12 carbon atoms, or 6 to 10 carbon atoms.

The term "aralkylene" refers to a divalent group that is an alkylene group substituted with an aryl group. The term "alkarylene" refers to a divalent group that is an arylene group substituted with an alkyl group or an arylene group attached to an alkylene group. For both groups, the alkyl or alkylene portion typically has from 1 to 20 carbon atoms, 1 to 10 carbon atoms, 1 to 6 carbon atoms, or 1 to 4 carbon atoms. For both groups, the aryl or arylene portion typically has from 6 to 20 carbon atoms, 6 to 18 carbon atoms, 6 to 16 carbon atoms, 6 to 12 carbon atoms, or 6 to 10 carbon atoms.

The term "heteroalkyl" includes both straight-chain, branched, and cyclic alkyl groups with one or more heteroatoms independently selected from S, O, and N, including both unsubstituted and substituted alkyl groups. Unless otherwise indicated, the heteroalkyl groups typically contain from 1 to 20 carbon atoms. "Heteroalkyl" is a subset of "hetero(hetero)hydrocarbyl" described below. Examples of "heteroalkyl" as used herein include, but are not limited to, methoxy, ethoxy, propoxy, 3,6-dioxaheptyl, 3-(trimethylsilyl)-propyl, 4-dimethylaminobutanyl, and the like. Unless otherwise noted, heteroalkyl groups may be mono- or polyvalent.

The term "hydrocarbyl" is inclusive of alkyl and aryl groups, including alkaryl and aralkyl.

The term "(hetero)hydrocarbyl" is inclusive of hydrocarbyl alkyl and aryl groups, and heterohydrocarbyl heteroalkyl and heteroaryl groups, the latter including one or more catenary oxygen heteroatoms such as ether or amino groups. Heterohydrocarbyl may optionally contain one or more catenary (in-chain) functional groups including ester, amide, urea, urethane, and carbonate functional groups. Unless otherwise indicated, the non-polymeric (hetero)hydrocarbyl groups typically contain from 1 to 60 carbon atoms and can optionally include substituents such as hydroxyl, chloro, amino, and carboxylic acid. Some examples of such (hetero) hydrocarbyls as used herein include, but are not limited to, methoxy, ethoxy, propoxy, 4-diphenylaminobutyl, 2-(2'-phenoxyethoxy)ethyl, 3,6-dioxaheptyl, 3,6-dioxahexyl-6-phenyl, in addition to those described for "alkyl," "heteroalkyl," "aryl," and "heteroaryl" described above.

The term "composite particle" as used herein refers to a nanoparticle, which is typically in the form of a core/shell nanoparticle (preferably, nanocrystal), having any associated organic coating or other material on the surface of the nanoparticle that is not removed from the surface by ordinary solvation. Such composite particles are useful as "quantum dots," which have a tunable emission in the near ultraviolet (UV) to far infrared (IR) range as a result of the use of a semiconductor material.

The term "nanoparticle" refers to a particle having an average particle diameter in the range of 0.1 to 1000 nanometers such as in the range of 0.1 to 100 nanometers or in the range of 1 to 100 nanometers. The term "diameter" refers not only to the diameter of substantially spherical particles but also to the distance along the smallest axis of the structure. Suitable techniques for measuring the average particle diameter include, for example, scanning tunneling microscopy, light scattering, and transmission electron microscopy.

A "core" of a nanoparticle is understood to mean a nanoparticle (preferably, a nanocrystal) to which no shell has been applied or to the inner portion of a core/shell nanoparticle. A core of a nanoparticle can have a homogenous composition or its composition can vary with depth inside the core. Many materials are known and used in core nanoparticles, and many methods are known in the art for applying one or more shells to a core nanoparticle. The core has a different composition than the one more shells. The core typically has a different chemical composition than the shell of the core/shell nanoparticle.

As used herein, the term "actinic radiation" refers to radiation in any wavelength range of the electromagnetic spectrum. The actinic radiation is typically in the ultraviolet wavelength range, in the visible wavelength range, in the infrared wavelength range, or combinations thereof. Any suitable energy source known in the art can be used to provide the actinic radiation.

BRIEF DESCRIPTION OF THE DRAWINGS

FIG. 3 is a schematic illustration of an embodiment of a display including a quantum dot article.

FIG. 4 is a schematic illustration of a white point measurement system.

DETAILED DESCRIPTION

Figure 1:
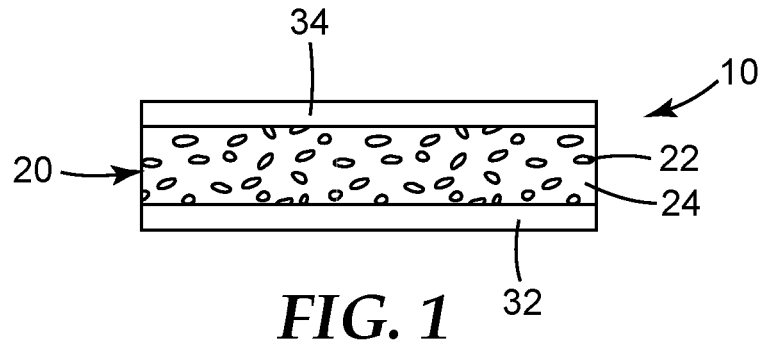
FIG. 1 is a schematic side elevation view of an edge region of an illustrative film article including quantum dots.

The present disclosure provides composite particles that contain fluorescent semiconductor nanoparticles that can fluoresce when excited with actinic radiation. The composite particles can be used in coatings and films for use in optical displays.

Fluorescent semiconductor nanoparticles emit a fluorescence signal when suitably excited. They fluoresce at a second wavelength of actinic radiation when excited by a first wavelength of actinic radiation that is shorter than the second wavelength. In some embodiments, the fluorescent semiconductor nanoparticles can fluoresce in the visible region of the electromagnetic spectrum when exposed to wavelengths of light in the ultraviolet region of the electromagnetic spectrum. In other embodiments, the fluorescent semiconductor nanoparticles can fluoresce in the infrared region when excited in the ultraviolet or visible regions of the electromagnetic spectrum. In still other embodiments, the fluorescent semiconductor nanoparticles can fluoresce in the ultraviolet region when excited in the ultraviolet region by a shorter wavelength of light, can fluoresce in the visible region when excited by a shorter wavelength of light in the visible region, or can fluoresce in the infrared region when excited by a shorter wavelength of light in the infrared region. The fluorescent semiconductor nanoparticles are often capable of fluorescing in a wavelength range such as, for example, at a wavelength up to 1200 nanometers (nm), or up to 1000 nm, up to 900 nm, or up to 800 nm. For example, the fluorescent semiconductor nanoparticles are often capable of fluorescence in the range of 400 to 800 nanometers.

The nanoparticles have an average particle diameter of at least 0.1 nanometer (nm), or at least 0.5 nm, or at least 1 nm. The nanoparticles have an average particle diameter of up to 1000 nm, or up to 500 nm, or up to 200 nm, or up to 100 nm, or up to 50 nm, or up to 20 nm, or up to 10 nm. Semiconductor nanoparticles, particularly with sizes on the scale of 1-10 nm, have emerged as a category of the most promising advanced materials for display technologies.

Semiconductor materials include elements or complexes of Group 2-Group 16, Group 12-Group 16, Group 13-Group 15, Group 14-Group 16, and Group 14 semiconductors of the Periodic Table (using the modern group numbering system of 1-18). Some suitable quantum dots include a metal phosphide, a metal selenide, a metal telluride, or a metal sulfide. Exemplary semiconductor materials include, but are not limited to, Si, Ge, Sn, BN, BP, BAs, AlN, AlP, AlAs, AlSb, GaN, GaP, GaAs, GaSb, InN, InP, InAs, InSb, AlN, AlP, AlAs, AlSb, GaN, GaP, GaAs, GaSb, ZnO, ZnS, ZnSe, ZnTe, CdS, CdSe, CdTe, HgS, HgSe, HgTe, BeS, BeSe, BeTe, MgS, MgSe, MgTe, GeS, GeSe, GeTe, SnS, SnSe, SnTe, PbO, PbS, Pb Se, PbTe, CuF, CuCl, CuBr, CuI, $Si_3N_4$, $Ge_3N_4$, $Al_2O_3$, $(Ga,In)_2(S,Se,Te)_3$, $Al_2CO$, CaS, CaSe, CaTe, SrS, SrSe, SrTe, BaS, BaSe, BaTe, and an appropriate combination of two or more such semiconductors. These semiconductor materials can be used for the core, the one or more shell layers, or both.

In certain embodiments, exemplary metal phosphide quantum dots include indium phosphide and gallium phosphide, exemplary metal selenide quantum dots include cadmium selenide, lead selenide, and zinc selenide, exemplary metal sulfide quantum dots include cadmium sulfide, lead sulfide, and zinc sulfide, and exemplary metal telluride quantum dots include cadmium telluride, lead telluride, and zinc telluride. Other suitable quantum dots include gallium arsenide and indium gallium phosphide. Exemplary semiconductor materials are commercially available from Evident Technologies (Troy, N.Y.).

Nanocrystals (or other nanostructures) for use in the present invention can be produced using any method known to those skilled in the art. Suitable methods are disclosed in WO2005/022120 (Scher et al.), U.S. Pat. No. 6,949,206 (Whiteford) and U.S. Pat. No. 7,267,875 (Whiteford et al.) the disclosures of each of which are incorporated by reference herein in their entireties. The nanocrystals (or other nanostructures) for use in the present invention can be produced from any suitable material, suitably an inorganic material, and more suitably an inorganic conductive or semiconductive material. Suitable semiconductor materials include those disclosed in WO2005/022120 (Scher et al.) and include any type of semiconductor, including group II-VI, group III-V, group IV-VI and group IV semiconductors.

Suitable semiconductor materials include, but are not limited to, Si, Ge, Sn, Se, Te, B, C (including diamond), P, BN, BP, BAs, AlN, AlP, AlAs, AlSb, GaN, GaP, GaAs, GaSb, InN, InP, InAs, InSb, AlN, AlP, As, AlSb, GaN, GaP, GaAs, GaSb, ZnO, ZnS, ZnSe, ZnTe, CdS, CdSe, CdTe, HgS, HgSe, HgTe, BeS, BeSe, BeTe, MgS, MgSe, GeS, GeSe, GeTe, SnS, SnSe, SnTe, PbO, PbS, PbSe, PbTe, CuF, CuCl, CuBr, CuI, $Si_3N_4$, $Ge_3N_4$, $Al_2O_3$, $(Ga, In)_2 (S, Se, Te)_3$, $Al_2CO$, and an appropriate combination of two or more such semiconductors.

In certain aspects, the semiconductor nanocrystals or other nanostructures may comprise a dopant from the group consisting of: a p-type dopant or an n-type dopant. The nanocrystals (or other nanostructures) useful in the present invention can also comprise II-VI or III-V semiconductors. Examples of II-VI or III-V semiconductor nanocrystals and nanostructures include any combination of an element from Group II, such as Zn, Cd and Hg, with any element from Group VI, such as S, Se, Te, Po, of the Periodic Table; and any combination of an element from Group III, such as B, Al, Ga, In, and Tl, with any element from Group V, such as N, P, As, Sb and Bi, of the Periodic Table.

Other suitable inorganic nanostructures include metal nanostructures. Suitable metals include, but are not limited to, Ru, Pd, Pt, Ni, W, Ta, Co, Mo, Ir, Re, Rh, Hf, Nb, Au, Ag, Ti, Sn, Zn, Fe, FePt, and the like.

While any known method can be used to create nanocrystal phosphors, suitably, a solution-phase colloidal method for controlled growth of inorganic nanomaterial phosphors is used. See Alivisatos, A. P., "Semiconductor clusters, nanocrystals, and quantum dots," Science 271:933 (1996); X. Peng, M. Schlamp, A. Kadavanich, A. P. Alivisatos, "Epitaxial growth of highly luminescent CdSe/CdS Core/Shell nanocrystals with photostability and electronic accessibility," J. Am. Chem. Soc. 30:7019-7029 (1997); and C. B. Murray, D. J. Norris, M. G. Bawendi, "Synthesis and characterization of nearly monodisperse CdE (E=sulfur, selenium, tellurium) semiconductor nanocrystallites," J. Am. Chem. Soc. 115:8706 (1993). This manufacturing process technology leverages low cost processability without the need for clean rooms and expensive manufacturing equipment. In these methods, metal precursors that undergo pyrolysis at high temperature are rapidly injected into a hot solution of organic surfactant molecules. These precursors break apart at elevated temperatures and react to nucleate nanocrystals. After this initial nucleation phase, a growth phase begins by the addition of monomers to the growing crystal. The result is freestanding crystalline nanoparticles in solution that have an organic surfactant molecule coating their surface.

As result of the preparation, the nanocrystal phosphors have a non-fluorinated ligand bound to the surface. Such ligands are of the general formula:

$$R^5\text{-}R^4(L^1)_n \qquad \text{III}$$

wherein
$R^5$ is (hetero)hydrocarbyl group having $C_2$ to $C_{30}$ carbon atoms;
$R^4$ is a a hydrocarbyl group including alkylene, arylene, alkarylene and aralkylene; n is at least one;
$L^1$ is a ligand group, including —$CO_2H$, —OH, —SH, —$P(O)(OH)_2$, —P(O)OH, —$NH_2$ and —$SO_3H$.

Such ligand groups are partially or fully displaced by the fluorochemical ligands of Formula I.

Utilizing this approach, synthesis occurs as an initial nucleation event that takes place over seconds, followed by crystal growth at elevated temperature for several minutes. Parameters such as the temperature, types of surfactants present, precursor materials, and ratios of surfactants to monomers can be modified so as to change the nature and progress of the reaction. The temperature controls the structural phase of the nucleation event, rate of decomposition of precursors, and rate of growth. The organic surfactant molecules mediate both solubility and control of the nanocrystal shape.

In semiconductor nanocrystals, photo-induced emission arises from the band edge states of the nanocrystal. The band-edge emission from nanocrystals competes with radiative and non-radiative decay channels originating from surface electronic states. X. Peng, et al., J. Am. Chem. Soc. 30:7019-7029 (1997). As a result, the presence of surface defects such as dangling bonds provide non-radiative recombination centers and contribute to lowered emission efficiency. An efficient and permanent method to passivate and remove the surface trap states is to epitaxially grow an inorganic shell material on the surface of the nanocrystal. X. Peng, et al., J. Am. Chem. Soc. 30:7019-7029 (1997). The shell material can be chosen such that the electronic levels are type I with respect to the core material (e.g., with a larger bandgap to provide a potential step localizing the electron and hole to the core). As a result, the probability of non-radiative recombination can be reduced.

Core-shell structures are obtained by adding organometallic precursors containing the shell materials to a reaction mixture containing the core nanocrystal. In this case, rather than a nucleation-event followed by growth, the cores act as the nuclei, and the shells grow from their surface. The temperature of the reaction is kept low to favor the addition of shell material monomers to the core surface, while preventing independent nucleation of nanocrystals of the shell materials. Surfactants in the reaction mixture are present to direct the controlled growth of shell material and ensure solubility. A uniform and epitaxially grown shell is obtained when there is a low lattice mismatch between the two materials. Additionally, the spherical shape acts to minimize interfacial strain energy from the large radius of curvature, thereby preventing the formation of dislocations that could degrade the optical properties of the nanocrystal system.

In suitable embodiments, ZnS can be used as the shell material using known synthetic processes, resulting in a high-quality emission. As above, if necessary, this material can be easily substituted, e.g., if the core material is modified. Additional exemplary core and shell materials are described herein and/or known in the art.

For many applications of quantum dots, two factors are typically considered in selecting a material. The first factor is the ability to absorb and emit visible light. This consideration makes InP a highly desirable base material. The second factor is the material's photoluminescence efficiency (quantum yield). Generally, Group 12-Group 16 quantum dots (such as cadmium selenide) have higher quantum yield than Group 13-Group 15 quantum dots (such as InP). The quantum yield of InP cores produced previously has been very low (<1%), and therefore the production of a core/shell structure with InP as the core and another semiconductor compound with higher bandgap (e.g., ZnS) as the shell has been pursued in attempts to improve the quantum yield.

Thus, the fluorescent semiconductor nanoparticles (i.e., quantum dots) of the present disclosure include a core and a shell at least partially surrounding the core. The core/shell nanoparticles can have two distinct layers, a semiconductor or metallic core and a shell surrounding the core of an insulating or semiconductor material. The core often contains a first semiconductor material and the shell often contains a second semiconductor material that is different than the first semiconductor material. For example, a first Group 12-Group 16 (e.g., CdSe) semiconductor material can be present in the core and a second Group 12-Group 16 (e.g., ZnS) semiconductor material can be present in the shell.

In certain embodiments of the present disclosure, the core includes a metal phosphide (e.g., indium phosphide (InP), gallium phosphide (GaP), aluminum phosphide (AlP)), a metal selenide (e.g., cadmium selenide (CdSe), zinc selenide (ZnSe), magnesium selenide (MgSe)), or a metal telluride (e.g., cadmium telluride (CdTe), zinc telluride (ZnTe)). In certain embodiments, the core includes a metal phosphide (e.g., indium phosphide) or a metal selenide (e.g., cadmium selenide). In certain preferred embodiments of the present disclosure, the core includes a metal phosphide (e.g., indium phosphide).

The shell can be a single layer or multilayered. In some embodiments, the shell is a multilayered shell. The shell can include any of the core materials described herein. In certain embodiments, the shell material can be a semiconductor material having a higher bandgap energy than the semiconductor core. In other embodiments, suitable shell materials can have good conduction and valence band offset with respect to the semiconductor core, and in some embodiments, the conduction band can be higher and the valence band can be lower than those of the core. For example, in certain embodiments, semiconductor cores that emit energy in the visible region such as, for example, CdS, CdSe, CdTe, ZnSe, ZnTe, GaP, InP, or GaAs, or near IR region such as, for example, InP, InAs, InSb, PbS, or PbSe may be coated with a shell material having a bandgap energy in the ultraviolet regions such as, for example, ZnS, GaN, and magnesium chalcogenides such as MgS, MgSe, and MgTe. In other embodiments, semiconductor cores that emit in the near IR region can be coated with a material having a bandgap energy in the visible region such as CdS or ZnSe.

Formation of the core/shell nanoparticles may be carried out by a variety of methods. Suitable core and shell precursors useful for preparing semiconductor cores are known in the art and can include Group 2 elements, Group 12 elements, Group 13 elements, Group 14 elements, Group 15 elements, Group 16 elements, and salt forms thereof. For example, a first precursor may include metal salt (M+X−) including a metal atom (M+) such as, for example, Zn, Cd, Hg, Mg, Ca, Sr, Ba, Ga, In, Al, Pb, Ge, Si, or in salts and a counter ion (X−), or organometallic species such as, for example, dialkyl metal complexes. The preparation of a coated semiconductor nanocrystal core and core/shell nanocrystals can be found in, for example, Dabbousi et al. (1997) *J. Phys. Chem. B* 101:9463, Hines et al. (1996) *J. Phys. Chem.* 100: 468-471, and Peng et al. (1997) *J. Amer. Chem. Soc.* 119:7019-7029, as well as in U.S. Pat. No. 8,283,412 (Liu et al.) and U.S. Pat. No. 8,901,333 (Tulsky et al.).

In certain preferred embodiments of the present disclosure, the shell includes a metal sulfide (e.g., zinc sulfide or cadmium sulfide). In certain embodiments, the shell includes a zinc-containing compound (e.g., zinc sulfide or zinc selenide). In certain embodiments, a multilayered shell includes an inner shell overcoating the core, wherein the inner shell includes zinc selenide and zinc sulfide. In certain embodiments, a multilayered shell includes an outer shell overcoating the inner shell, wherein the outer shell includes zinc sulfide.

In some embodiments, the core of the shell/core nanoparticle contains a metal phosphide such as indium phosphide, gallium phosphide, or aluminum phosphide. The shell contains zinc sulfide, zinc selenide, or a combination thereof. In some more particular embodiments, the core contains indium phosphide and the shell is multilayered with the inner shell containing both zinc selenide and zinc sulfide and the outer shell containing zinc sulfide.

The thickness of the shell(s) may vary among embodiments and can affect fluorescence wavelength, quantum yield, fluorescence stability, and other photostability characteristics of the nanocrystal. The skilled artisan can select the appropriate thickness to achieve desired properties and may modify the method of making the core/shell nanoparticles to achieve the appropriate thickness of the shell(s).

The diameter of the fluorescent semiconductor nanoparticles (i.e., quantum dots) of the present disclosure can affect the fluorescence wavelength. The diameter of the quantum dot is often directly related to the fluorescence wavelength. For example, cadmium selenide quantum dots having an average particle diameter of about 2 to 3 nanometers tend to fluoresce in the blue or green regions of the visible spectrum while cadmium selenide quantum dots having an average particle diameter of about 8 to 10 nanometers tend to fluoresce in the red region of the visible spectrum.

The fluorescent semiconductor nanoparticles are surface-modified with a surface modifying agent to enhance their dispersibility in a liquid. That is, the surface modifying agent tends to increase compatibility of the fluorescent semiconductor nanoparticles with a fluorinated carrier fluid, and any other components of a composition (e.g., a polymeric material, precursors of the polymeric material, or combinations thereof).

Surface modification involves combining the fluorescent semiconductor nanoparticles with a surface modifying agent or combination of surface modifying agents that attach to the surface of the fluorescent semiconductor nanoparticles and that modify the surface characteristics of the fluorescent semiconductor nanoparticles. In this context, "attach" or "attached" refers to the association between the surface modifying agent and the fluorescent semiconductor nanoparticle, which is of sufficient stability for the surface modified particles to be suitable for their intended use. The association may be physical (e.g., by absorption or adsorption), chemical (e.g., through covalent bonds, ionic bonds, hydrogen bonds), or a combination thereof.

Surface modifying agents include one or more groups for attaching to the surface of the fluorescent semiconductor nanoparticles and one or more group for various functions, such as compatibilizing the particles with a solvent or carrier fluid, improving the quantum yield of the material. The groups attach to the surface, for example, by adsorption, absorption, formation of an ionic bond, formation of a covalent bond, formation of a hydrogen bond, or a combination thereof.

Quantum efficiency (also known in the literature as quantum yield) is the number of defined events which occur per photon absorbed (e. g., the number of photons emitted by the nanoparticles per photon absorbed by the nanoparticles). Accordingly, one general embodiment of the present disclosure provides a population of nanoparticles that displays a quantum efficiency of 45% or greater, or 50% or greater, or 55% or greater, or 60% or greater.

Surface modifying agents useful in the present disclosure are fluoroether ligands of Formula I as previously described:

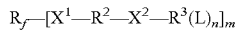

wherein
$R_f$ is a perfluoroether group,
$R^2$ is a hydrocarbyl group including alkylene, arylene, alkarylene and aralkylene;
$R^3$ is a hydrocarbyl group including alkylene, arylene, alkarylene and aralkylene;
$X^1$ is $—CH_2—O—$, $—O—$, $—S—$, $—CO_2—$, $—CONR^1—$, or $—SO_2NR^{1-}$ where $R^1$ is H or $C_1$-$C_4$ alkyl;
$X^2$ is a covalent bond, $—S—$, $—O—$ or $—NR^1—CO_2—$, $—CONR^1—$, or $—SO_2NR^{1-}$ where $R^1$ is H or $C_1$-$C_4$ alkyl;
n at least one;
m is 1 or 2
L is an ligand group selected from $—CO_2H$, $—SH$, $—P(O)(OH)_2$, $—P(O)OH$, $—NH_2—OH$, and $—SO_3H$.

The $R_f$ groups can be linear, branched and are of the formula:

$C_aF_{2a+1}—(O—C_bF_{2b})_c—$, (if monovalent), or $—C_aF_{2a}—(O—C_bF_{2b})_c—$ (if divalent), where a is at least 1, preferably 1-10, more preferably 2-6;
b is at least 1, preferably 1-10, more preferably 2-6, and c may be a number from 1 to 30.

The perfluoropolyether group $R_f$ may be cyclic or acyclic, linear or branched, or combinations thereof and can be saturated or unsaturated. The perfluoroether has at least one catenated (in-chain) oxygen heteroatoms.

Exemplary perfluoropolyethers include, but are not limited to, those that have perfluorinated repeating units selected from the group of $—(C_pF_{2p})—$, $—(C_pF_{2p}O)—$, $—(CF(Z))—$, $—(CF(Z)O)—$, $—(CF(Z)C_pF_{2p}O)—$, $—(C_pF_{2p}CF(Z)O)—$, $—(CF_2CF(Z)O)—$, or combinations thereof. In these repeating units, p is typically an integer of 1 to 10. In some embodiments, p is an integer of 1 to 8, 1 to 6, 1 to 4, 1 to 3, or 1 to 2. The group Z is a fluorine atom, perfluoroalkyl group, perfluoroether group, nitrogen-containing perfluoroalkyl group, perfluoropolyether, or a perfluoroalkoxy group, all of which can be linear, branched, or cyclic. The Z group typically has no more than 12 carbon atoms, no more than 10 carbon atoms, or no more than 9 carbon atoms, no more than 4 carbon atoms, no more than 3 carbon atoms, no more than 2 carbon atoms, or no more than 1 carbon atom. In some embodiments, the Z group can have no more than 4, no more than 3, no more than 2, no more than 1, or no oxygen atoms. In these perfluoropolyether structures, the different repeat units can be distributed randomly along the chain.

Suitable structures for $R_f$ groups include, but are not limited to, $R_f'$—$CF_2O(CF_2O)_q(C_2F_4O)_rCF_2$—, $R_f'$—$(CF_2)_3O(C_4F_8O)_r(CF_2)_3$—, $R_f'$—$CF_2O(C_2F_4O)_rCF_2$—, and $R_f'$—$CF(CF_3)(OCF_2CF(CF_3))_sOC_tF_{2t}O(CF_2O)_sCF(CF_3)$—, wherein $R_f'$ is F or a perfluoroalkyl group; q has an average value of 0 to 50, 1 to 50, 3 to 30, 3 to 15, or 3 to 10; r has an average value of 0 to 50, 3 to 30, 3 to 15, or 3 to 10; s has an average value of 0 to 50, 1 to 50, 3 to 30, 3 to 15, or 3 to 10; the sum (r+s) has an average value of 1 to 50 or 4 to 40; the sum (q+r) is greater than 0; and t is an integer of 2 to 6.

As synthesized, compounds typically include a mixture of $R_f$ groups. The average structure is the structure averaged over the mixture components. The values of q, r, and s in these average structures can vary, as long as the compound has a number average molecular weight of at least about 300. Useful compounds often have a molecular weight (number average) of 400 to 5000, 800 to 4000, or 1000 to 5000.

Preferably, $R_f$ is the oligomer of hexafluoropropylene oxide (HFPO) with a number average molecular weight at least 1,000.

Prep of Ligands

The ligands may be prepared from a perfluoroether ester, such as $R_f$—$CO_2CH_3$. The ester can be reacted with an amine or hydroxyl functional compound to provide the ligands of Formula I, where $X^1$ is an ester, thioester or amide:

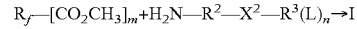

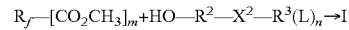

Alternatively, the ester can be reacted with a olefin having a nucleophic groups, such as an amine, and the resulting compound functionalized by an ene reaction:

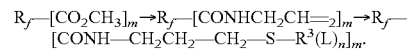

Alternatively, the ester can be reacted with a nucleophilic thiol compound, then further functionalized by an ene reaction:

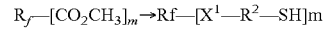

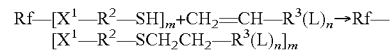

The ester can be reduced to a hydroxyl group, facilitating preparation of compounds having a $—CH_2—OH$ "$X^1$"

group. This in turn may be reacted with a vinyl halide, such as allyl bromide to provide a terminal unsaturation, which in turn may be functionalized by an ene reaction, where m is 1 or 2:

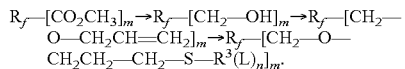

Alternatively, a perfluoropolyether acid fluoride may be reacted with fluoride ion to produce an intermediate having a nucleophilic —$CF_2$—$O^-$ group. The intermediate may be functionalized with a terminal olefin, such as with allyl bromide, or reacted with a compound of the formula Y—$R^2$—$X^2$—$R^3(L)_n$, where Y is a leaving group, such as halide or tosylate:

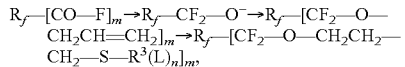

or

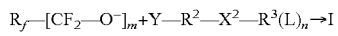

A dispersion of the ligand functionalized nanoparticles composition may also include a fluorinated carrier fluid. Preferably the dispersion comprises a fluorinated carrier fluid. The fluorinated carrier fluid are typically selected to be compatible (i.e., miscible) with the surface modifying agent added to the surface of the fluorescent semiconductor nanoparticles. The ligand functionalized nanoparticles and fluorinated carrier fluid form a coating that is colorless and transparent when viewed with the human eye. Likewise, any precursors of the polymeric materials that are included in the dispersion composition are soluble in a fluorinated carrier fluid and form a coating that is colorless and transparent when viewed with the unaided human eye. The term transparent means transmitting at least 85% of incident light in the visible spectrum (about 400-700 nm wavelength). The term colorless means having a CIELAB b* less than about 1.5 units, preferably less than about 1.0 unit for samples with thickness of 500 microns.

As the quantum dots are often prepared and ligand-functionalized in an organic solvent, the fluorinated carrier fluid enables separation and removal of any organic solvent.

The optional fluorinated, carrier fluids are inert, liquid at 25° C. and have a boiling point ≥100° C., preferably ≥150° C.; and can be one or a mixture of perfluorinated or highly fluorinated liquid compounds having, in some embodiments, at least 8 carbon atoms or more, and optionally containing one or more catenary heteroatoms, such as divalent oxygen, hexavalent sulfur, or trivalent nitrogen and having a hydrogen content of less than 5 percent by weight or less than 1 percent by weight. Higher boiling points are preferred so that the carrier fluids remain when organic solvents used in the preparation are removed.

Suitable fluorinated, inert fluids useful of the present disclosure include, for example, perfluoroalkanes or perfluorocycloalkanes, such as, perfluorooctane, perfluorononane, perfluorodecane, perfluorotetradecahydrophenanthrene, perfluorodecalin, and perfluoromethyldecalin; perfluoroamines, such as, perfluorotripentyl amine, perfluorotributyl amine, perfluorotripropyl amine, perfluorotriamyl amine, and perfluoro-N-isopropyl morpholine; perfluoroethers, such as $HCF_2(OCF(CF_3)CF_2)_sOCF_2CF_2H$, $HCF_2(OCF(CF_3)CF_2)_s$—$(OCF_2)_q$—$OCF_2H$, (where subscripts s and q are as defined for the fluorinated ligand compounds), perfluorobutyl tetrahydrofuran, perfluorodibutyl ether, perfluorobutoxyethoxy formal, perfluorohexyl formal, and perfluorooctyl formal; perfluoropolyethers; hydrofluorocarbons, such as pentadecafluorohydroheptane, 1, 1,2,2-tetrafluorocyclobutane, 1-trifluoromethyl-1,2,2-trifluorocyclobutane and 2-hydro-3-oxaheptadecafluorooctane.

In some embodiments, the ligand functional quantum dots are added to the fluid carrier in amounts such that the optical density is at least 10, optical density defined as the absorbance at 440 nm for a cell with a path length of 1 cm) solution.

The surface-modified, fluorescent semiconductor nanoparticles may be dispersed in a solution, suspension or dispersion that contains (a) a fluorinated carrier fluid and (b) a polymeric binder, a precursor of the polymeric binder, or combinations thereof. The ligand functionalized nanoparticles may be dispersed in the carrier fluid, which is then dispersed in the polymeric binder, forming droplets of the nanoparticles in the carrier, fluid, which in turn are dispersed in the polymeric binder.

The polymeric binders desirably provide barrier properties to exclude oxygen and moisture. If water and/or oxygen enter the quantum dot article, the quantum dots can degrade and ultimately fail to emit light when excited by ultraviolet or blue light irradiation. Slowing or eliminating quantum dot degradation along the laminate edges is particularly important to extend the service life of the displays in smaller electronic devices such as those utilized in, for example, handheld devices and tablets.

Exemplary polymeric materials include, but are not limited to, polysiloxanes, fluoroelastomers, polyamides, polyimides, caprolactones, caprolactams, polyurethanes, polyvinyl alcohols, polyvinyl chlorides, polyvinyl acetates, polyesters, polycarbonates, polyacrylates, polymethacrylates, polyacrylamides, and polymethacrylamides. Suitable precursors of the polymeric material (i.e., precursor materials) include any precursor materials used to prepare the polymeric materials listed above. Exemplary precursor materials include acrylates that can be polymerized to polyacrylates, methacrylates that can be polymerized to form polymethacrylates, acrylamides that can be polymerized to form polyacrylamides, methacrylamides that can be polymerized to form polymethacrylamides, epoxy resins and dicarboxylic acids that can be polymerized to form polyesters, diepoxides that can be polymerized to form polyethers, isocyanates and polyols that can be polymerized to form polyurethanes, or polyols and dicarboxylic acids that can be polymerized to form polyesters.

In some embodiments, the polymeric binder is a thermally curable epoxy-amine composition optionally further comprising a radiation-curable acrylate as described in Applicant's copending WO 2015095296 (Eckert et al.); Thiol-epoxy resins as described in U.S. 62/148,219 (Qiu et al., filed 16 Apr. 2015), thiol-alkene-epoxy resins as described in U.S. 62/148,212 (Qui et al. filed 16 Apr. 2015); thiol-alkene resins as described in U.S. 62/080,488 (Qui et al., filed 17 Nov. 2014), and thiol silicones as described in U.S. 61/950,281 (Qiu et al., filed 10 Mar. 2014.

The quantum dot layer can have any useful amount of quantum dots, and in some embodiments the quantum dot layer can include from 0.1 to 10 wt %, preferably 0.1 to 1 wt %, quantum dots, based on the total weight of the quantum dot layer (dots, optional liquid carrier and polymeric binder). The dispersion composition can also contain a surfactant (i.e., leveling agent), a polymerization initiator, and other additives, as known in the art.

In some embodiments, the ligand functional quantum dots are added to the fluid carrier in amounts such that the optical density is at least 10, optical density defined as the absorbance at 440 nm for a cell with a path length of 1 cm) per mL solution.

Generally, the ligand-functional quantum dots, the polymeric binder and optional fluorinated carrier fluid solvent are combined and subject to high shear mixing to produce a dispersion of the ligand functional quantum dots in the polymer matrix. The matrix is chosen such there is limited compatibility and the quantum dots form a separate, non-aggregating phase in the matrix. As the quantum dots are often prepared and ligand-functionalized in an organic solvent, the fluorinated carrier fluid enables separation and removal of any organic solvent.

The dispersion, comprising droplets of ligand-functional nanoparticle dispersed in the binder resin, is then coated and cured either thermally, free-radically, or both to lock in the dispersed structure and exclude oxygen and water from the dispersed quantum dots.

When using a free-radically curable polymeric binder, the curable composition further comprises photoinitiators, in an amount between the range of about 0.1% and about 5% by weight.

Useful photoinitiators include those known as useful for photocuring free-radically polyfunctional (meth)acrylates. Exemplary photoinitiators include benzoin and its derivatives such as alpha-methylbenzoin; alpha-phenylbenzoin; alpha-allylbenzoin; alpha-benzylbenzoin; benzoin ethers such as benzil dimethyl ketal (e.g., "IRGACURE 651" from BASF, Florham Park, N.J.), benzoin methyl ether, benzoin ethyl ether, benzoin n-butyl ether; acetophenone and its derivatives such as 2-hydroxy-2-methyl-1-phenyl-1-propanone (e.g., "DAROCUR 1173" from BASF, Florham Park, N.J.) and 1-hydroxycyclohexyl phenyl ketone (e.g., "IRGACURE 184" from BASF, Florham Park, N.J.); 2-methyl-1-[4-(methylthio)phenyl]-2-(4-morpholinyl)-1-propanone (e.g., "IRGACURE 907" from BASF, Florham Park, N.J.); 2-benzyl-2-(dimethylamino)-1-[4-(4-morpholinyl)phenyl]-1-butanone (e.g., "IRGACURE 369" from BASF, Florham Park, N.J.) and phosphine oxide derivatives such as Ethyl-2,4,6-trimethylbenzoylphenylphoshinate (e.g. "TPO-L" from BASF, Florham Park, N.J.), and Irgacure 819 (phenylbis(2,4,6-trimethylbenzoyl)phosphine oxide) available from BASF, Florham Park, N.J.

Other useful photoinitiators include, for example, pivaloin ethyl ether, anisoin ethyl ether, anthraquinones (e.g., anthraquinone, 2-ethylanthraquinone, 1-chloroanthraquinone, 1,4-dimethylanthraquinone, 1-methoxyanthraquinone, or benzanthraquinone), halomethyltriazines, benzophenone and its derivatives, iodonium salts and sulfonium salts, titanium complexes such as bis(eta$_5$-2,4-cyclopentadien-1-yl)-bis[2,6-difluoro-3-(1H-pyrrol-1-yl)phenyl]titanium (e.g., "CGI 784DC" from BASF, Florham Park, N.J.); halomethyl-nitrobenzenes (e.g., 4-bromomethylnitrobenzene), mono- and bis-acylphosphines (e.g., "IRGACURE 1700", "IRGACURE 1800", "IRGACURE 1850", and "DAROCUR 4265").

The curable composition may be irradiated with activating UV or visible radiation to polymerize the components preferably in the wavelengths of 250 to 500 nanometers. UV light sources can be of two types: 1) relatively low light intensity sources such as blacklights that provide generally 10 mW/cm$^2$ or less (as measured in accordance with procedures approved by the United States National Institute of Standards and Technology as, for example, with a UVIMAP™ UM 365 L-S radiometer manufactured by Electronic Instrumentation & Technology, Inc., in Sterling, Va.) over a wavelength range of 280 to 400 nanometers and 2) relatively high light intensity sources such as medium- and high-pressure mercury arc lamps, electrodeless mercury lamps, light emitting diodes, mercury-xenon lamps, lasers and the like, which provide intensities generally between 10 and 5000 mW/cm$^2$ in the wavelength rages of 320-390 nm (as measured in accordance with procedures approved by the United States National Institute of Standards and Technology as, for example, with a PowerPuck™ radiometer manufactured by Electronic Instrumentation & Technology, Inc., in Sterling, Va.).

Referring to FIG. 1, quantum dot article 10 includes a first barrier layer 32, a second barrier layer 34, and a quantum dot layer 20 between the first barrier layer 32 and the second barrier layer 34. The quantum dot layer 20 includes a plurality of quantum dots 22 dispersed in a matrix 24.

The barrier layers 32, 34 can be formed of any useful material that can protect the quantum dots 22 from exposure to environmental contaminates such as, for example, oxygen, water, and water vapor. Suitable barrier layers 32, 34 include, but are not limited to, films of polymers, glass and dielectric materials. In some embodiments, suitable materials for the barrier layers 32, 34 include, for example, polymers such as polyethylene terephthalate (PET); oxides such as silicon oxide, titanium oxide, or aluminum oxide (e.g., $SiO_2$, $Si_2O_3$, $TiO_2$, or $Al_2O_3$); and suitable combinations thereof.

More particularly, barrier films can be selected from a variety of constructions. Barrier films are typically selected such that they have oxygen and water transmission rates at a specified level as required by the application. In some embodiments, the barrier film has a water vapor transmission rate (WVTR) less than about 0.005 g/m$^2$/day at 38° C. and 100% relative humidity; in some embodiments, less than about 0.0005 g/m$^2$/day at 38° C. and 100% relative humidity; and in some embodiments, less than about 0.00005 g/m$^2$/day at 38° C. and 100% relative humidity. In some embodiments, the flexible barrier film has a WVTR of less than about 0.05, 0.005, 0.0005, or 0.00005 g/m$^2$/day at 50° C. and 100% relative humidity or even less than about 0.005, 0.0005, 0.00005 g/m$^2$/day at 85° C. and 100% relative humidity. In some embodiments, the barrier film has an oxygen transmission rate of less than about 0.005 g/m$^2$/day at 23° C. and 90% relative humidity; in some embodiments, less than about 0.0005 g/m$^2$/day at 23° C. and 90% relative humidity; and in some embodiments, less than about 0.00005 g/m$^2$/day at 23° C. and 90% relative humidity.

Exemplary useful barrier films include inorganic films prepared by atomic layer deposition, thermal evaporation, sputtering, and chemical vapor deposition. Useful barrier films are typically flexible and transparent. In some embodiments, useful barrier films comprise inorganic/organic. Flexible ultra-barrier films comprising inorganic/organic multilayers are described, for example, in U.S. Pat. No. 7,018,713 (Padiyath et al.). Such flexible ultra-barrier films may have a first polymer layer disposed on polymeric film substrate that is overcoated with two or more inorganic barrier layers separated by at least one second polymer layer. In some embodiments, the barrier film comprises one inorganic barrier layer interposed between the first polymer layer disposed on the polymeric film substrate and a second polymer layer 224.

In some embodiments, each barrier layer 32, 34 of the quantum dot article 10 includes at least two sub-layers of different materials or compositions. In some embodiments, such a multi-layered barrier construction can more effectively reduce or eliminate pinhole defect alignment in the barrier layers 32, 34, providing a more effective shield against oxygen and moisture penetration into the matrix 24. The quantum dot article 10 can include any suitable material or combination of barrier materials and any suitable number of barrier layers or sub-layers on either or both sides of the quantum dot layer 20. The materials, thickness, and number of barrier layers and sub-layers will depend on the particular application, and will suitably be chosen to maximize barrier protection and brightness of the quantum dots 22 while minimizing the thickness of the quantum dot article 10. In some embodiments each barrier layer 32, 34 is itself a laminate film, such as a dual laminate film, where each barrier film layer is sufficiently thick to eliminate wrinkling in roll-to-roll or laminate manufacturing processes. In one illustrative embodiment, the barrier layers 32, 34 are polyester films (e.g., PET) having an oxide layer on an exposed surface thereof.

The quantum dot layer 20 can include one or more populations of quantum dots or quantum dot materials 22. Exemplary quantum dots or quantum dot materials 22 emit green light and red light upon down-conversion of blue primary light from a blue LED to secondary light emitted by the quantum dots. The respective portions of red, green, and blue light can be controlled to achieve a desired white point for the white light emitted by a display device incorporating the quantum dot article 10. Exemplary quantum dots 22 for use in the quantum dot articles 10 include, but are not limited to, CdSe with ZnS shells. Suitable quantum dots for use in quantum dot articles described herein include, but are not limited to, core/shell luminescent nanocrystals including CdSe/ZnS, InP/ZnS, PbSe/PbS, CdSe/CdS, CdTe/CdS or CdTe/ZnS. In exemplary embodiments, the luminescent nanocrystals include an outer ligand coating and are dispersed in a polymeric matrix. Quantum dot and quantum dot materials 22 are commercially available from, for example, Nanosys Inc., Milpitas, Calif. The quantum dot layer 20 can have any useful amount of quantum dots 22, and in some embodiments the quantum dot layer 20 can include from 0.1 wt % to 1 wt % quantum dots, based on the total weight of the quantum dot layer 20.

In some embodiments, the quantum dot materials can include quantum dots dispersed in a liquid carrier. For example, the liquid carrier can include an oil such as an amino-silicone oil.

In one or more embodiments the quantum dot layer 20 can optionally include scattering beads or particles. These scattering beads or particles have a refractive index that differs from the refractive index of the matrix material 24 by at least 0.05, or by at least 0.1. These scattering beads or particles can include, for example, polymers such as silicone, acrylic, nylon, and the like, or inorganic materials such as $TiO_2$, $SiO_x$, $AlO_x$, and the like, and combinations thereof. In some embodiments, including scattering particles in the quantum dot layer 20 can increase the optical path length through the quantum dot layer 20 and improve quantum dot absorption and efficiency. In many embodiments, the scattering beads or particles have an average particle size from 1 to 10 micrometers, or from 2 to 6 micrometers. In some embodiments, the quantum dot material 20 can optionally include fillers such fumed silica.

In some preferred embodiments, the scattering beads or particles are Tospearl™ 120A, 130A, 145A and 2000B spherical silicone resins available in 2.0, 3.0, 4.5 and 6.0 micron particle sizes respectively from Momentive Specialty Chemicals Inc., Columbus, Ohio.

The matrix 24 of the quantum dot layer 20 can be formed from an polymeric binder or binder precursor that adheres to the materials forming the barrier layers 32, 34 to form a laminate construction, and also forms a protective matrix for the quantum dots 22. In one embodiment, the matrix 24 is formed by curing or hardening an adhesive composition including an epoxy amine polymer and an optional radiation-curable methacrylate compound.

Figure 2:
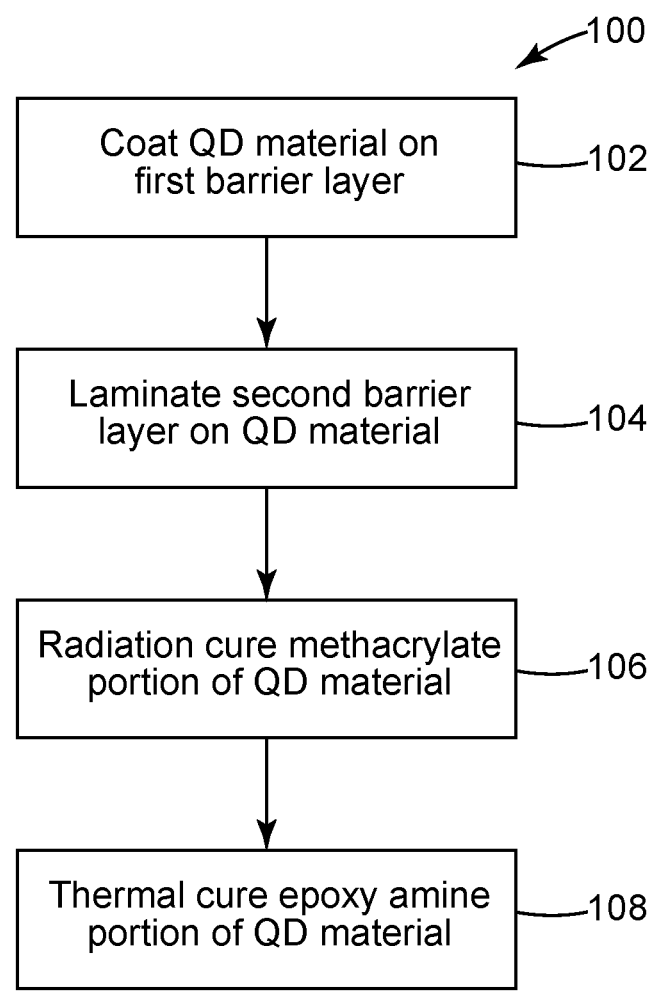
FIG. 2 is a flow diagram of an illustrative method of forming a quantum dot film.

Referring to FIG. 2, in another aspect, the present disclosure is directed to a method of forming a quantum dot film article 100 including coating an adhesive composition including quantum dots on a first barrier layer 102 and disposing a second barrier layer on the quantum dot material 104. In some embodiments, the method 100 includes polymerizing (e.g., radiation curing) the radiation curable methacrylate compound to form a partially cured quantum dot material 106 and polymerizing the binder composition to form a cured matrix 108.

In some embodiments, the binder composition can be cured or hardened by heating. In other embodiments, the adhesive composition may also be cured or hardened by applying radiation such as, for example, ultraviolet (UV) light. Curing or hardening steps may include UV curing, heating, or both. In some example embodiments that are not intended to be limiting, UV cure conditions can include applying about 10 $mJ/cm^2$ to about 4000 $mJ/cm^2$ of UVA, more preferably about 10 $mJ/cm^2$ to about 200 $mJ/cm^2$ of UVA. Heating and UV light may also be applied alone or in combination to increase the viscosity of the binder composition, which can allow easier handling on coating and processing lines.

In some embodiments, the binder composition may be cured after lamination between the overlying barrier films 32, 34. Thus, the increase in viscosity of the binder composition locks in the coating quality right after lamination. By curing right after coating or laminating, in some embodiments the cured binder increases in viscosity to a point that the binder composition acts as a pressure sensitive adhesive (PSA) to hold the laminate together during the cure and greatly reduces defects during the cure. In some embodiments, the radiation cure of the binder provides greater control over coating, curing and web handling as compared to traditional thermal curing.

Once at least partially cured, the binder composition forms polymer network that provides a protective supporting matrix 24 for the quantum dots 22.

Ingress, including edge ingress, is defined by a loss in quantum dot performance due to ingress of moisture and/or oxygen into the matrix 24. In various embodiments, the edge ingress of moisture and oxygen into the cured matrix 24 is less than about 1.25 mm after 1 week at 85° C., or about less than 0.75 mm after 1 week at 85° C., or less than about 0.5 mm after 1 week at 85° C. In various embodiments, oxygen permeation into the cured matrix is less than about 80 (cc·mil)/($m^2$ day), or less than about 50 (cc·mil)/($m^2$ day). In various embodiments, the water vapor transmission rate of the cured matrix should be less than about 15 (20 $g/m^2$·mil·day), or less than about 10 (20 $g/m^2$·mil·day).

In various embodiments, the thickness of the quantum dot layer 20 is about 80 microns to about 250 microns.

FIG. 3 is a schematic illustration of an embodiment of a display device 200 including the quantum dot articles described herein. This illustration is merely provided as an example and is not intended to be limiting. The display device 200 includes a backlight 202 with a light source 204 such as, for example, a light emitting diode (LED). The light source 204 emits light along an emission axis 235. The light source 204 (for example, a LED light source) emits light through an input edge 208 into a hollow light recycling cavity 210 having a back reflector 212 thereon. The back reflector 212 can be predominately specular, diffuse or a combination thereof, and is preferably highly reflective. The backlight 202 further includes a quantum dot article 220, which includes a protective matrix 224 having dispersed therein quantum dots 222. The protective matrix 224 is bounded on both surfaces by polymeric barrier films 226, 228, which may include a single layer or multiple layers.

The display device 200 further includes a front reflector 230 that includes multiple directional recycling films or layers, which are optical films with a surface structure that redirects off-axis light in a direction closer to the axis of the display, which can increase the amount of light propagating on-axis through the display device, this increasing the brightness and contrast of the image seen by a viewer. The front reflector 230 can also include other types of optical films such as polarizers. In one non-limiting example, the front reflector 230 can include one or more prismatic films 232 and/or gain diffusers. The prismatic films 232 may have prisms elongated along an axis, which may be oriented parallel or perpendicular to an emission axis 235 of the light source 204. In some embodiments, the prism axes of the prismatic films may be crossed. The front reflector 230 may further include one or more polarizing films 234, which may include multilayer optical polarizing films, diffusely reflecting polarizing films, and the like. The light emitted by the front reflector 230 enters a liquid crystal (LC) panel 280. Numerous examples of backlighting structures and films may be found in, for example, U.S. Pat. No. 8,848,132 (O'Neill et al.).

Various composite particles are provided.

Embodiment 1 is a composite particle comprising: a fluorescent semiconductor core/shell nanoparticle; and the ligand of Formula I attached to the core/shell nanoparticle outer surface Embodiment 2 is the composite particle of embodiment 1 wherein the core comprises a first semiconductor material and the shell comprises a second semiconductor material that is different than the first semiconductor material.

Embodiment 3 is the composite particle of embodiment 1 or 2 wherein the core comprises a metal phosphide or a metal selenide.

Embodiment 4 is the composite particle of embodiment 3 wherein the core comprises InP or CdSe.

Embodiment 5 is the composite particle of any of embodiments 1 through 4 wherein the shell comprises a zinc-containing compound.

Embodiment 6 is the composite particle of any of embodiments 1 through 5 wherein the shell is a multilayered shell.

Embodiment 7 is the composite particle of embodiment 6 wherein the multilayered shell comprises an inner shell overcoating the core, wherein the inner shell comprises zinc selenide and zinc sulfide.

Embodiment 8 is the composite particle of embodiment 7 wherein the multilayered shell comprises an outer shell overcoating the inner shell, wherein the outer shell comprises zinc sulfide.

Embodiment 9 is the composite particle of any of embodiments 1 through 8 dispersed in a fluorinated carrier fluid in an amount of at least 1 wt-%.

Embodiment 10 is the composite particle comprising: a fluorescent semiconductor core/shell nanoparticle comprising: an InP core; an inner shell overcoating the core, wherein the inner shell comprises zinc selenide and zinc sulfide; and an outer shell overcoating the inner shell, wherein the outer shell comprises zinc sulfide; and a ligand of Formula I attached to the core/shell nanoparticle outer surface.

Various quantum dot articles are further provided;

Embodiment 11 is a quantum dot film article comprising:
a first barrier layer;
a second barrier layer; and
a quantum dot layer between the first barrier layer and the second barrier layer, the quantum dot layer comprising quantum dots dispersed in a binder matrix.

Embodiment 12 is the article of embodiment 11 wherein the binder matrix comprises a cured composition, wherein the composition comprises polysiloxanes, fluoroelastomers, polyamides, polyimides, caprolactones, caprolactams, polyurethanes, polyvinyl alcohols, polyvinyl chlorides, polyvinyl acetates, polyesters, polycarbonates, polyacrylates, polymethacrylates, polyacrylamides, and polymethacrylamides.

Embodiment 13 is the article of any one of embodiments 11-12, wherein the binder composition further comprises a photoinitator.

Embodiment 14 is the article of any one of embodiments 11-13, wherein the matrix further comprises scattering particles having an average size in a range from 1 to 10 micrometers.

Embodiment 15 is the film article of any one of embodiments 11-14, wherein at least one of the first and the second barrier layer comprises at least one polymeric film.

Embodiment 16 is a display device comprising the film article of any one of embodiments 11-15.

Embodiment 17 is a method of forming a article, comprising coating a quantum dot material on a first polymeric barrier film, the quantum dot material comprising quantum dots in an uncured binder composition.

Embodiment 18 is the method of embodiment 17, further comprising curing the binder composition.

Embodiment 19 is the method of embodiment 18, further comprising applying a second polymeric barrier film on the binder composition.

The following examples are provided to further illustrate the present invention and are not intended to limit the invention in any manner.

EXAMPLES

Materials

| Material | Description |
| --- | --- |
| Quantum Dots | Obtained from Nanosys, Inc (Milpitas, CA). "Green growth solution" describes a dispersion of green-emitting InP quantum dots with a zinc sulfide shell dispersed in octadecene with an optical density of 10. "Red growth solution" describes a similar dispersion of red-emitting quantum dots, also with an optical density of 10. The quantum dot dispersions were stored and handled in an inert atmosphere glove box. |
| Krytox 1506 | a perfluorinated polymer oil manufactured by DuPont (Wilmington, DE) and obtained from Sigma Aldrich (St Louis, MO) under trade designation "KRYTOX 1506". This material was degassed with bubbling nitrogen and stored in an inert atmosphere glove box. |
| FC-70 | A high-boiling perfluorinated fluid available from 3M 3M (St. Paul, MN) under trade designation "FLUORINERT ELECTRONIC LIQUID FC-70." |
| PF-5052 | a fully fluorinated solvent available from 3M (St. Paul, MN) under trade designation "PERFORMANCE FLUID PF-5052". |
| Novec 7100 | a hydrofluoroether solvent available from 3M (St. Paul, MN) under trade designation "NOVEC 7100 ENGINEERED FLUID." |
| Novec 7200 | a hydrofluoroether solvent available from 3M (St. Paul, MN) under trade designation "NOVEC 7200 ENGINEERED FLUID." |

-continued

| Material | Description |
|---|---|
| Heptane | anhydrous grade obtained from Sigma Aldrich (St. Louis, MO) and was stored in an inert atmosphere glove box. |
| Barrier Film | 2 mil (50 micrometer) barrier film obtained as FTB-M-50 from 3M, St. Paul, MN |
| CN2003B | modified epoxy acrylate available from Sartomer USA, LLC (Exton, PA) under trade designation "CN2003B" |
| SR833 | tricyclodecane dimethanol diacrylate available from Sartomer USA, LLC (Exton, PA) under trade designation "SR833". |
| TPO-L | liquid photoinitiator available from BASF Resins (Wyandotte, Michigan) under trade designation "IRGACURE TPO-L". |
| TEMPIC | Tris[2-(3-mercaptopropionyloxy)ethyl] Isocyanurate available form Bruno Bock Chemische Fabrik GmbH & Co. KG (Marschacht, Germany) |
| TAIC | Triallyl Isocyanurate available from TCI America (Portland, Oregon). |

All other reagents and chemicals were obtained from standard chemical suppliers and were used as received.

Test Methods

% Transmission was measured using a Byk HazeGuard Plus (Columbia, Md.).

Edge ingress was tested by placing the coatings on a black light and then measuring how much of the edge of the film is dark (does not illuminate) with a ruler.

External quantum efficiency (EQE) was measured by using an absolute PL Quantum Yield Spectrometer C11347 (Hamamatsu Corporation, Middlesex, N.J.).

White point (color) was quantified by placing the constructed QDEF film into a recycling system (FIG. 4) and measuring with a colorimeter (available from Photo Research, Inc., Chatsworth, Calif., under the trade designation "PR650"). A gain cube with a blue LED light was used with the QDEF film, which contained red and green quantum dots, and a pair of crossed micro-replicated brightness enhancement film (available from 3M, St. Paul, Minn., under the trade designation "VIKUITI BEF"). White point measurements were quantified using the CIE1931 (x,y) convention.

Preparative Example 1: Preparation of HFPO-Derived Methyl Ester

The methyl ester $F(CF(CF_3)CF_2O)_aCF(CF_3)C(O)OCH_3$, wherein the variable a has an average value of about 6, was prepared by metal fluoride-initiated oligomerization of hexafluoropropylene oxide in diglyme solvent according to the method described in U.S. Pat. No. 3,250,808 (Moore et al.), the description of which is incorporated herein by reference. The product was purified by distillation to remove low-boiling components.

Preparative Example 2: Preparation of HFPO-Derived Allyl Ether

The allyl ether $F(CF(CF_3)CF_2O)_aCF(CF_3)CH_2OCH_2CHCH2$, wherein the variable a has an average value of about 6, was prepared from the methyl ester of Preparative Example 1 by sodium borohydride reduction to the alcohol followed by allylation with allyl bromide according to the method described in US Patent Application No. 2014-0287248 (Flynn et. al.), the description of which is incorporated herein by reference.

Example 1: Preparation of HFPO-Derived Allyl Amine

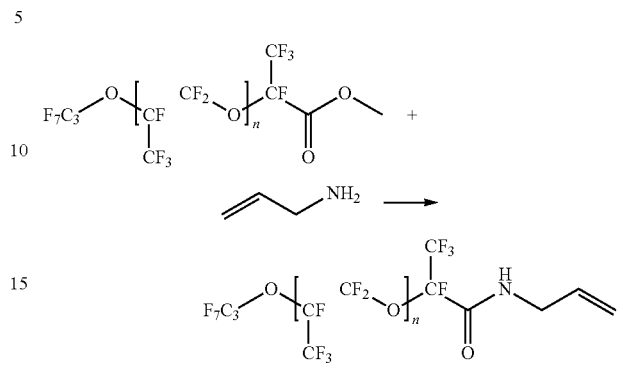

A flask with condenser attached was charged with the methyl ester of Preparative Example 1 (200 g, 150 mmol) and allyl amine (13.2 g, 231 mmol). The resulting 2-phase suspension was heated with stirring in an oil bath held at 80° C. Within 30 min, the 2-phase suspension turned into a clear solution. After 3 hours of heating, the solution was cooled and then diluted with 150 mL of PF-5052. This solution was washed 3 times with 100 mL of aqueous 1M HCl. The fluorinated phase was dried over $Na_2SO_4$, filtered, and concentrated at reduced pressure to yield a clear, viscous liquid obtained in near quantitative yield.

Example 2: Preparation of HFPO-Derived Amide Succinic Acid

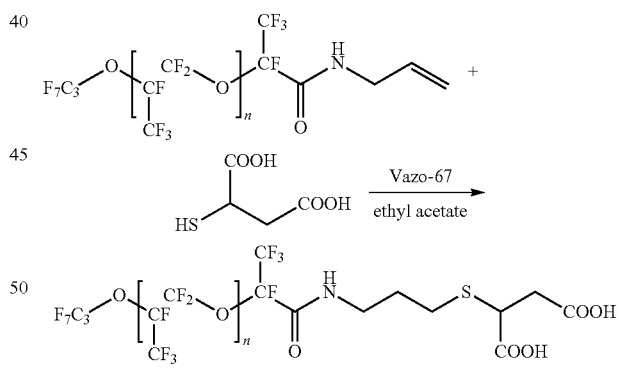

A flask with condenser attached was charged with the polymer of Example 1 (100. g, 80.0 mmol), ethyl acetate (400 mL), mercaptosuccinic acid (18 g, 120 mmol), and Vazo-67 (2.3 g, 12 mmol). The mixture was deoxygenated by bubbling $N_2$ through the liquid for 15 min. The solution was then heated to reflux and stirred overnight. The solvent was removed by rotary evaporation at reduced pressure, and the product was dissolved in 300 mL of PF-5052. The solution was washed three times with 350 mL of a 5:2 isopropanol:water mixture (by volume). The solvent was removed by rotary evaporation at reduced pressure to yield 108.5 g of light yellow waxy solid (97% yield).

Example 3: Preparation of HFPO-Derived Ether Succinic Acid

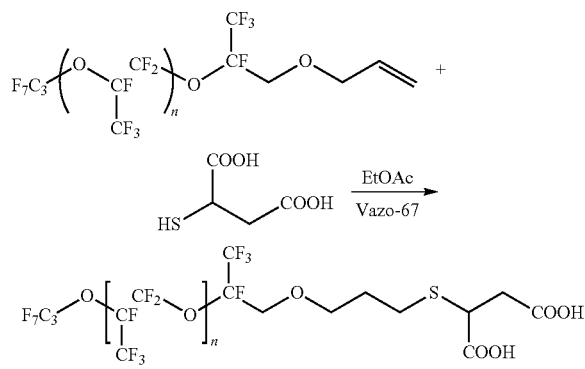

A flask with condenser attached was charged with the polymer of Preparative Example 2 (5.0 g, 3.5 mmol), ethyl acetate (20 mL), mercaptosuccinic acid (0.79 g, 5.3 mmol), and Vazo-67 (100 mg, 0.53 mmol). The mixture was deoxygenated by bubbling $N_2$ through the liquid for 15 min. The solution was then heated to reflux and stirred overnight. The solvent was removed by rotary evaporation at reduced pressure, and the product was dissolved in 50 mL of PF-5052. The solution was washed three times with 70 mL of a 5:2 isopropanol:water mixture (by volume). The solvent was removed by rotary evaporation at reduced pressure to yield 4.5 g of clear viscous oil.

Example 4: Preparation of HFPO-Derived Ether Thioester

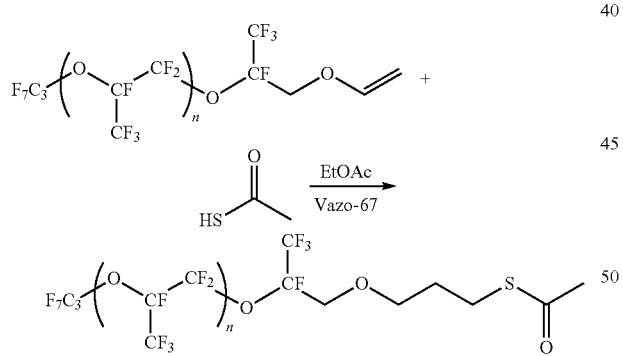

A flask with condenser attached was charged with the polymer of Preparative Example 2 (20.0 g, 14.0 mmol), ethyl acetate (50 mL), Novec 7100 (30 mL), thioacetic acid (1.60 g, 21.0 mmol), and Vazo-67 (400 mg, 2.1 mmol). The mixture was deoxygenated by bubbling $N_2$ through the liquid for 15 min. The solution was then heated at reflux and stirred overnight. The solvent was removed by rotary evaporation at reduced pressure, and the product was dissolved in 100 mL of PF-5052. The solution was washed three times with 140 mL of a 5:2 isopropanol:water mixture (by volume). The solvent was removed by rotary evaporation at reduced pressure to yield 19 g of clear oil.

Example 5: Preparation of HFPO-Derived Ether Thiol

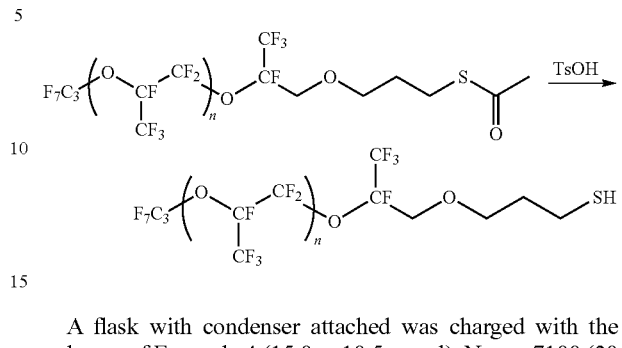

A flask with condenser attached was charged with the polymer of Example 4 (15.0 g, 10.5 mmol), Novec 7100 (20 mL), methanol (10 mL), and p-toluenesulfonic acid (2.0 g, 10.5 mmol). The solution was heated at reflux overnight. The solvent was removed by rotary evaporation at reduced pressure, and the product was dissolved in 50 mL of PF-5052 the solution was washed three times with 50 mL of isopropanol. The solvent was removed by rotary evaporation at reduced pressure to yield 14 g of clear oil.

Example 6: Preparation of a Green InP/ZnS Quantum Dot Dispersion in Perfluorinated Oil In an inert atmosphere glovebox, a 1000 mL round bottomed flask was charged with 20.4 g of the HFPO-derived succinic acid polymer of Example 2, 93.0 g of Krytox 1506, and 374 mL of green growth solution. The flask was fitted with an overhead stirrer and placed on a hot plate held at 80° C. The mixture was stirred vigorously for 3 hours, after which it was allowed to cool and separate into 2 layers overnight. The orange-green color of the quantum dots had transferred completely into the lower perfluorinated phase. The clear top layer was removed, and the perfluorinated layer was washed 4 times with 150 mL of heptane. Each washing involved 10 min of vigorous stirring, followed by 2 to 12 hours to allow the layers to fully separate. After all four washings, residual heptane was removed at low pressure. The oil was filtered through a 5 micron syringe filter, yielding an orange/green oil with low haze and an optical density (OD) of approximately 60.

Example 7: Preparation of a Mixed Red and Green InP/ZnS Quantum Dot Dispersion in Perfluorinated Oil In an inert atmosphere glovebox, a 250 mL round bottomed flask was charged with 9.83 g of the HFPO-derived succinic acid polymer of Example 2, 24.6 mL of Krytox 1506, 60 mL of green growth solution and 60 mL of red growth solution. The flask was fitted with an overhead stirrer and placed on a hot plate held at 80° C. The mixture was stirred vigorously for 2 hours, after which it was allowed to cool and separate into 2 layers overnight. The orange-brown color of the quantum dots had transferred completely into the lower perfluorinated phase. The clear top layer was removed, and the perfluorinated layer was washed 4 times with 50 mL of heptane. Each washing involved 10 min of vigorous stirring, followed by 2 to 12 hours to allow the layers to fully separate. After all four washings, residual heptane was removed at low pressure, yielding an orange/brown oil with low haze and an OD of approximately 40. For quantum yield measurements, approximately 10 µL of solution was diluted in 4 mL of Krytox 1506.

Example 8: Preparation of a Green InP/ZnS Dispersion with FC-70 as the Diluent A mixture of 20 g of the polymer of Example 3 and 40 g of FC-70 was degassed using bubbling nitrogen and then placed in an inert atmosphere glovebox. A 250 mL round bottomed flask was charged with 15 mL of the above solution and 120 mL of green growth solution. The flask was fitted with an overhead stirrer and placed on a hot plate held at 80° C. The mixture was stirred vigorously for 1 hour, after which it was allowed to cool and separate into 2 layers. The colorless top layer was removed, and the bottom fluorinated layer was washed twice with 30 mL of heptane, stirring for 5 minutes during each washing. Residual heptane was removed under low pressure, yielding a clear orange-green oil with an OD of approximately 80.

Example 9: Preparation of a Green InP/ZnS Dispersion with HFPO Thiol Ligands In an inert atmosphere glovebox, a vial was charged with 0.4 mL of the polymer of Example 5, 0.4 mL of PF-5052, and 2.0 mL of green growth solution. The vial was placed on a hot plate held at 80° C. and the biphasic mixture was stirred for 15 minutes. After cooling the clear top layer was removed yielding a perfluorinated dispersion with an OD of 25.

Comparative Example 1: Ligand Exchange with Dodecenylsuccinic Acid (DDSA) on Green InP In an inert atmosphere glovebox, a vial was charged with 2 mL of green InP growth solution, 40 mg of dodecenylsuccinic acid, and 80 mg of lauric acid. The resulting solution was stirred for 2 hours on a hot plate held at 80° C. After cooling, 24 µL of this solution was diluted with 4 mL of heptane for quantum yield measurement.

Comparative Example 2: Ligand Exchange with Dodecenylsuccinic Acid (DDSA) on 1:1 Red:Green InP In an inert atmosphere glovebox, a vial was charged with 1 mL of green InP growth solution, 1 mL of red InP growth solution, 40 mg of dodecenylsuccinic acid, and 80 mg of lauric acid. The resulting solution was stirred for 2 hours on a hot plate held at 80° C. After cooling, 24 µL of this solution was diluted with 4 mL of heptane for quantum yield measurement.

Comparative optical data were collected on the quantum dot dispersions of the two unmodified dispersions, Examples 6 and 7, and Comparative Examples 1 and 2. The data are shown in Table 1.

TABLE 1

Solution Optical Data of InP Quantum Dot Dispersions

| Quantum Dot Dispersion | Quantum Yield | Peak Wavelength(s) | Full Width at Half Maximum |
| --- | --- | --- | --- |
| Green Growth Solution | 82.7% | 529 nm | 45 nm |
| Red Growth Solution | 74.6% | 609 nm | 50 nm |
| Example 6 | 80.6% | 530 nm | 42 nm |
| Example 7 | 73.7% | 530 nm, 612 nm | 49 nm (red peak) |
| Comparative Example 1 | 82.5% | 529 nm | 44 nm |
| Comparative Example 2 | 79.3% | 529 nm, 611 nm | 49 nm (red peak) |

Example 10: Preparation of a White InP Concentrate in Perfluorinated Oil

The green InP solution of Example 6 was combined with the 1:1 red:green InP solution of Example 7 in the relative amounts shown in Table 2 to prepare Solution A.

TABLE 2

Solution A - White InP Quantum Dot Concentrate in Perfluorinated Oil

| Material | Weight % |
| --- | --- |
| Green InP in perfluorinated oil at OD = 60 (Example 6) | 53.8% |
| 1:1 Green:Red InP in perfluorinated oil at OD = 40 (Example 7) | 46.2% |
| SUM | 100.0% |

Example 11: Preparation of QDEF using an Acrylate Matrix and InP Quantum Dots in Perfluorinated Oil To prepare an acrylate matrix formulation, termed Solution B, the components shown in Table 3 were added together, heated in a microwave for 20 seconds, and then left on a shaker overnight until uniformly mixed.

TABLE 3

Solution B - Acrylate Matrix

| Material | Weight % |
| --- | --- |
| CN2003B | 49.7% |
| SR833 | 49.7% |
| TPO-L | 0.7% |
| Sum | 100.00% |

Dot concentrate (solution A) was added to the acrylate matrix (solution B) at 7.83 wt %. The solution of dot concentrate and matrix was mixed with a cowles blade for 3 minutes at 1400 rpm. This mixture was coated between two 2 mil (50 micrometers) barrier films at a thickness of 100 micrometers using a knife coater. The coatings were cured with ultraviolet (UV) radiation using a Clearstone UV LED lamp at 385 nm for 60 seconds.

Example 12: Preparation of QDEF using a Thiol-ene Matrix and InP Quantum Dots in Perfluorinated Oil Procedures followed were identical to that of Example 11, except Solution C, the formulation of which is shown in Table 4, was substituted for Solution B.

TABLE 4

| Solution C - Thiol-ene Matrix | |
| --- | --- |
| Material | Weight % |
| TEMPIC | 63.9% |
| TAIC | 35.5% |
| TPO-L | 0.6% |
| Sum | 100.00% |

Example 13: Accelerated Aging Tests of QDEF Samples

Coatings were tested initially, after 1 week of aging at 85° C. and after 1 week of aging in a lifetime screening box (aged at a temperature of 85° C. and a light intensity of 152 watts/sr/m²). Initial results are shown in Table 6. One week 85° C. aging results are shown in Table 7. Lifetime screening box results are shown in Table 8.

TABLE 6

| Optical Characterization of QDEF Coatings | | | | | |
| --- | --- | --- | --- | --- | --- |
| Example | Matrix | % transmission | Luminance (cd/m²) | X | Y | EQE |
| 11 | Solution B | 66.2 | 299.6 | 0.2309 | 0.2169 | 66.2% |
| 12 | Solution C | 67.7 | 325.4 | 0.2465 | 0.2386 | 68.7% |

TABLE 7

| Performance Change of QDEF Coatings After Aging for 1 Week at 85° C. | | | | | |
| --- | --- | --- | --- | --- | --- |
| Example | Matrix | ΔLuminance (%) | Δ X, Y | Edge Ingress (mm) | Δ EQE (%) |
| 11 | Solution B | −1.64 | 0.008 | 0.00 | −6.4% |
| 12 | Solution C | −10.00 | 0.019 | 0.25 | −8.0% |

TABLE 8

| Performance Change After Accelerated Aging in the Lifetime Screening Box | | | | |
| --- | --- | --- | --- | --- |
| Example | Matrix | ΔLuminance (%) | Δ x | Δ y | Δ x, y |
| 11 | Solution B | −0.3% | 0.0110 | −0.0123 | 0.0165 |
| 12 | Solution C | 2.4% | 0.0095 | −0.0113 | 0.0147 |

What is claimed is:

1. A composite particle comprising a fluorescent core/shell nanoparticle and a fluoroether ligand bound to the surface of the nanoparticle of the formula:

$$R_f—[X^1—R^2—X^2—R^3(L)_n]_m$$

wherein
$R_f$ is a perfluoroether group,
$R^2$ is a hydrocarbyl group including alkylene, arylene, alkarylene and aralkylene;
$R^3$ is a hydrocarbyl group including alkylene, arylene, alkarylene and aralkylene;
$X^1$ is —CH$_2$—O—, —O—, —S—, —CO$_2$—, —CONR$^1$—, or —SO$_2$NR$^{1-}$ where R$^1$ is H or C$_1$-C$_4$ alkyl;
$X^2$ is a covalent bond, —S—, —O— or —NR$_1$—, —CO$_2$—, —CONR$^1$—, or —SO$_2$NR$^{1-}$ where R$^1$ is H or C$_1$-C$_4$ alkyl;
n at least one;
m is 1 or 2
L is an ligand group selected from —CO$_2$H, —SH, —P(O)(OH)$_2$, —P(O)OH, —NH$_2$, —OH, and —SO$_3$H.

2. The composite particle of claim 1 wherein there are at least two L groups.

3. The composite particle of claim 1 wherein R$^2$ is a C$_1$-C$_{20}$ alkylene or an arylene.

4. The composite particle of claim 1 wherein R$_f$ is of the formula C$_a$F$_{2a+1}$—(O—C$_b$F$_{2b}$)$_c$—, where a is at least 1, b is at least 1 and c may be a number from 1 to 10.

5. The composite particle of claim 1 wherein R$_f$ is of the formula —C$_a$F$_{2a}$—(O—C$_b$F$_{2b}$)$_c$—, where a is at least 1, b is at least 1 and c may be a number from 1 to 10.

6. The composite particle of claim 4 wherein each of subscripts a and b are 1 to 6.

7. The composite particle of claim 1 further comprising a non-fluorochemical ligand bound to the surface of the nanoparticle of the formula:

$$R^5-R^4(L^1)_n \qquad \text{III}$$

wherein
R$^5$ is (hetero)hydrocarbyl group having C$_2$ to C$_{30}$ carbon atoms;
R$^4$ is a a hydrocarbyl group including alkylene, arylene, alkarylene and aralkylene;
n is at least one;
L$^1$ is a ligand group.

8. The composite particle of claim 1 wherein the ligand is of the formula:

$$R_f—X^1—R^2—S—CH(CO_2H)CH_2CO_2H$$

wherein
R$_f$ is a perfluoroether group,
R$^2$ is a hydrocarbyl group including alkylene, arylene, alkarylene and aralkylene, and
X$^1$ is —CH$_2$—O—, —O—, —S—, —CO$_2$—, —CONR$^1$—, or —SO$_2$NR$^{1-}$ where R$^1$ is H or C$_1$-C$_4$ alkyl.

9. The composite particle of claim 1, further comprising a fluid carrier.

10. The composite particle of claim 1 wherein the core comprises InP, CdS or CdSe, and wherein the shell comprises a magnesium or zinc-containing compound.

11. The composite particle of claim 1 comprising:
a fluorescent semiconductor core/shell nanoparticle comprising:
an InP core;
an inner shell overcoating the core, wherein the inner shell comprises zinc selenide and zinc sulfide; and
an outer shell overcoating the inner shell, wherein the outer shell comprises zinc sulfide; and
a fluorinated ligand bound to the surface of the nanoparticle, the fluorinated ligand of the formula:

$$R_f—[X^1—R^2—X^2—R^3(L)_n]_m$$

wherein
R$_f$ is a perfluoroether group,
R$^2$ is a hydrocarbyl group including alkylene, arylene, alkarylene and aralkylene;
R$^3$ is a hydrocarbyl group including alkylene, arylene, alkarylene and aralkylene;
X$^1$ is —CH$_2$—O—, —O—, —S—, —CO$_2$—, —CONR$^1$—, or —SO$_2$NR$^{1-}$ where R$_1$ is H or C$_1$-C$_4$ alkyl;

$X^2$ is a covalent bond, —S—, —O— or —NR'—, —$CO_2$—, —$CONR^1$—, or —$SO_2NR^{1-}$ where $R^1$ is H or $C_1$-$C_4$ alkyl;
n at least one;
m is 1 or 2
L is an ligand group selected from –$CO_2H$, —SH, —P(O)(OH)$_2$, —P(O)OH, —$NH_2$—OH, and —$SO_3H$.

12. A composition comprising the composite particle of claim 1 and a polymeric binder.

13. The composition of embodiment 25 wherein the binder comprises polysiloxanes, fluoroelastomers, polyamides, polyimides, caprolactones, caprolactams, polyurethanes, polyvinyl alcohols, polyvinyl chlorides, polyvinyl acetates, polyesters, polycarbonates, polyacrylates, polymethacrylates, polyacrylamides, and polymethacrylamides.

14. An article comprising a quantum dots layer comprising the composite particle of claim 12 dispersed in a polymeric matrix binder, the layer between two barrier films.

15. The article of claim 14 comprising from 0.1 wt % to 1 wt % ligand functional particles, based on the total weight of the quantum dot layer (dots, optional liquid carrier and polymeric binder).

16. An article comprising a quantum dot layer between two barrier films, the quantum dot layer comprising the composite particles of claim 1 in a polymer binder.

17. The article of claim 16 wherein the composite particle further comprise a fluorinated fluid carrier, dispersed in a polymer binder.

18. A dispersion comprising the composite particles of claim 1 in a fluorinated carrier fluid.

19. The dispersion of claim 18 wherein the fluorinated carrier fluid is selected from perfluoroalkanes or perfluorocycloalkanes, perfluoroamines; perfluoroethers; perfluoropolyethers; and hydrofluorocarbons.

20. A quantum dot film article comprising:
a first barrier layer;
a second barrier layer; and
a quantum dot layer between the first barrier layer and the second barrier layer, the quantum dot layer comprising the composite particles of claim 1, the composite particles dispersed in droplets of a fluorinated liquid carrier, and the droplets dispersed in a polymeric resin matrix.

21. The quantum dot film article of claim 20 wherein the quantum dot layer comprises dispersed droplets of ligand functional quantum dots in a fluorinated carrier liquid.

* * * * *

UNITED STATES PATENT AND TRADEMARK OFFICE
CERTIFICATE OF CORRECTION

PATENT NO. : 10,767,108 B2
APPLICATION NO. : 15/745749
DATED : September 8, 2020
INVENTOR(S) : Paul Armstrong It is certified that error appears in the above-identified patent and that said Letters Patent is hereby corrected as shown below:

On the Title Page

Column 2 (Abstract),
Line 2, after "bound" insert -- to --.

Second Page, Column 2 (Other Publications),
Line 25, delete "Perfluoropolycther-Coated" and insert -- Perfluoropolyether-Coated --, therefor.

In the Specification

Column 1,
Line 51, before "—$CO_2$—," insert -- —$O_2$—, --.
Line 51, delete "—$SO_2NR^{1\text{-}}$" and insert -- —$SO_2NR^1$— --, therefor.
Line 53, after "—$NR^1$—," insert -- -$CO_2$-, --.
Line 54, delete "—$SO_2NR^{1\text{-}}$" and insert -- —$SO_2NR^1$— --, therefor.
Line 56, after "n" insert -- is --.

Column 2,
Line 47, delete "benzthiazolyl." and insert -- benzothiazolyl. --, therefor.

Column 6,
Line 30, delete "a a" and insert -- a --, therefor.

Column 9,
Line 45, delete "—$SO_2NR^{1\text{-}}$" and insert -- —$SO_2NR^1$— --, therefor.
Line 47, delete "—$SO_2NR^{1\text{-}}$" and insert -- —$SO_2NR^1$— --, therefor.
Line 49, after "n" insert -- is --.

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*

Column 10,
Line 22, delete "O(CF$_2$O)$_S$" and insert -- O(CF(CF$_3$)CF$_2$O)$_S$ --, therefor.
Line 54, delete "nucleophic" and insert -- nucleophilic --, therefor.
Line 56 (approx.), delete "=$_2$]$_m$" and insert -- =CH$_2$]$_m$ --, therefor.
Line 65 (approx.), after "(L)$_n$]$_m$" insert -- . --.

Column 11,
Line 22 (approx.), after "(L)$_n$ →I" insert -- . --.

Column 12,
Line 57, delete "2014." and insert -- 2014). --, therefor.

Column 17,
Line 36, after "surface" insert -- . --.

In the Claims

Column 25,
Line 66, in Claim 1, delete "—SO$_2$NR$^{1\text{-}}$" and insert -- —SO$_2$NR$^1$— --, therefor.

Column 26,
Line 1, in Claim 1, delete "—NR$_1$—," and insert -- —NR$^1$—, --, therefor.
Line 2, in Claim 1, delete "—SO$_2$NR$^{1\text{-}}$" and insert -- —SO$_2$NR$^1$— --, therefor.
Line 4, in Claim 1, after "n" insert -- is --.
Line 28, in Claim 7, delete "a a" and insert -- a --, therefor.
Line 41, in Claim 8, delete "—SO$_2$NR$^{1\text{-}}$" and insert -- —SO$_2$NR$^1$— --, therefor.
Line 67, in Claim 11, delete "—SO$_2$NR$^{1\text{-}}$" and insert -- —SO$_2$NR$^1$— --, therefor.
Line 67, in Claim 11, delete "R$_1$" and insert -- R$^1$ --, therefor.

Column 27,
Line 1, in Claim 11, delete "—NR'—," and insert -- —NR$^1$—, --, therefor.
Line 2, in Claim 11, delete "—SO$_2$NR$^{1\text{-}}$" and insert -- —SO$_2$NR$^1$— --, therefor.
Line 3, in Claim 11, after "n" insert -- is --.
Line 9, in Claim 13, delete "embodiment 25" and insert -- claim 12 --, therefor.